US008753555B2

(12) United States Patent
Rizk et al.

(10) Patent No.: US 8,753,555 B2
(45) Date of Patent: *Jun. 17, 2014

(54) MEDICAL DEVICES CONTAINING ORIENTED FILMS OF POLY-4-HYDROXYBUTYRATE AND COPOLYMERS

(75) Inventors: Said Rizk, Salem, NH (US); David P. Martin, Arlington, MA (US); Kicherl Ho, Groton, MA (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/084,388

(22) Filed: Apr. 11, 2011

(65) Prior Publication Data

US 2011/0189475 A1   Aug. 4, 2011

Related U.S. Application Data

(63) Continuation of application No. 11/931,850, filed on Oct. 31, 2007, now Pat. No. 7,943,683.

(60) Provisional application No. 60/868,182, filed on Dec. 1, 2006.

(51) Int. Cl.
| *B29C 55/04* | (2006.01) |
| *B29C 55/12* | (2006.01) |
| *A61L 27/18* | (2006.01) |
| *A61L 27/58* | (2006.01) |
| *C08L 67/04* | (2006.01) |
| *C08G 63/08* | (2006.01) |

(52) U.S. Cl.
USPC ... 264/210.7; 523/113; 523/115; 264/177.17; 264/211.12; 528/354; 428/336

(58) Field of Classification Search
USPC .............. 523/113, 115; 528/354; 264/177.17, 264/211.12, 210.7; 428/336
See application file for complete search history.

(56) References Cited

U.S. PATENT DOCUMENTS

| 3,598,122 A | 8/1971 | Zaffaroni |
| 3,598,123 A | 8/1971 | Zaffaroni |
| 3,731,683 A | 5/1973 | Zaffaroni |
| 3,797,494 A | 3/1974 | Zaffaroni |
| 3,982,543 A | 9/1976 | Schmitt |
| 4,031,894 A | 6/1977 | Urquhart |
| RE30,170 E | 12/1979 | Goodman |
| 4,201,211 A | 5/1980 | Chandrasekaran |
| 4,205,399 A | 6/1980 | Shataby |
| 4,286,592 A | 9/1981 | Chandrasekaran |
| 4,314,557 A | 2/1982 | Chandrasekaran |
| 4,379,454 A | 4/1983 | Campbell |
| 4,435,180 A | 3/1984 | Leeper |
| 4,537,738 A | 8/1985 | Holmes |
| 4,559,222 A | 12/1985 | Enscore |
| 4,573,995 A | 3/1986 | Chen |
| 4,588,580 A | 5/1986 | Gale |
| 4,603,070 A | 7/1986 | Steel |
| 4,645,502 A | 2/1987 | Gale |
| 4,648,978 A | 3/1987 | Makinen |
| 4,664,655 A | 5/1987 | Orentreich |
| 4,704,282 A | 11/1987 | Campbell |
| 4,711,241 A | 12/1987 | Lehmann |
| 4,743,257 A | 5/1988 | Tormala |
| 4,758,234 A | 7/1988 | Orentreich |
| 4,788,062 A | 11/1988 | Gale |
| 4,792,336 A | 12/1988 | Hlavacek |
| 4,816,258 A | 3/1989 | Nedberge |
| 4,826,493 A | 5/1989 | Martini |
| 4,849,226 A | 7/1989 | Gale |
| 4,853,226 A | 8/1989 | Machida |
| 4,856,188 A | 8/1989 | Sibalis |
| 4,876,331 A | 10/1989 | Doi |
| 4,880,592 A | 11/1989 | Martini |

(Continued)

FOREIGN PATENT DOCUMENTS

| CA | 2307637 | 5/1999 |
| CA | 2259098 | 7/1999 |

(Continued)

OTHER PUBLICATIONS

Abate, et al., 'Separation and structural characterizations of cyclic and open chain oligomers produced in the partial pyrolysis ofmicrobial poly(hydroxyutyrates)', Macromolecules,#s(28#23):7911-1916 (1996).

Abate,et al., "Thermal Degradatuion of Microbial Poly(4-hydrixybutyrate)", Macromolecules, 27:332-336 (1994).

Addolorato, et al., 'Maintaining abstinence from alcohol with gamma-hydroxybutyric acid', The Lancet, 351:38(1998).

Agostini, et al., 'Synthesis and characterization of poly-(3-hydroxybutyrate. I. Synthesis of crystallineDL-poly-13-hydroxybutyrate from DL-0-butyrolactone' Journal of Polymer Science, Part A-1, 9: 2775-2787(1971).

Akhtar, 'Physiomechanical Properties of bacterial P(HB-FIV) Polyesters and Their Uses in drug Delivery,' The BritishLibrary Document Supply Centre, UMI, (1990).

(Continued)

*Primary Examiner* — Tae H Yoon
(74) *Attorney, Agent, or Firm* — Pabst Patent Group LLP

(57) ABSTRACT

Continuous processing methods for making absorbable polymeric films with one or more of the following properties: high toughness, low modulus, high tensile strength, and thickness less than 10 mm, more preferably less than 1 mm, and more preferably less than 100 μm, have been developed. In the preferred embodiment, the polymer is a polyhydroxyalkanoate, and in the most preferred embodiment, the polymer comprises 4-hydroxybutyrate. A particularly preferred embodiment is a film of poly-4-hydroxybutyrate or copolymer thereof, wherein the film has a tensile strength greater than 5.5 kgf/mm², tensile modulus less than 181 kgf/mm², and elongation at break from 10-500%, wherein the film is derived by a continuous process such as melt extrusion or solvent casting, followed by orientation to more than 25% of the film's original length in one or more directions. These can be used for a variety of purposes including fabrication of medical devices.

18 Claims, No Drawings

(56) References Cited

U.S. PATENT DOCUMENTS

| | | |
|---|---|---|
| 4,908,027 A | 3/1990 | Enscore |
| 4,910,145 A | 3/1990 | Holmes |
| 4,938,763 A | 7/1990 | Dunn |
| 4,943,435 A | 7/1990 | Baker |
| 4,968,317 A | 11/1990 | Tormala |
| 5,002,067 A | 3/1991 | Berthelsen |
| 5,026,381 A | 6/1991 | Li |
| 5,032,638 A | 7/1991 | Wang |
| 5,041,100 A | 8/1991 | Rowland |
| 5,085,629 A | 2/1992 | Goldberg |
| 5,124,371 A | 6/1992 | Tokiwa |
| 5,128,144 A | 7/1992 | Korsatko-Wabnegg et al. |
| 5,171,308 A | 12/1992 | Gallagher |
| 5,204,382 A | 4/1993 | Wallace |
| 5,236,431 A | 8/1993 | Gogolewski |
| 5,245,023 A | 9/1993 | Peoples |
| 5,250,430 A | 10/1993 | Peoples |
| 5,271,961 A | 12/1993 | Mathiowitz |
| 5,278,201 A | 1/1994 | Dunn |
| 5,278,202 A | 1/1994 | Dunn |
| 5,278,256 A | 1/1994 | Bellis |
| 5,288,516 A | 2/1994 | Anderson |
| 5,292,860 A | 3/1994 | Shiotani |
| 5,306,286 A | 4/1994 | Stack |
| 5,334,698 A | 8/1994 | Witholt |
| 5,386,004 A | 1/1995 | Obuchi |
| 5,443,458 A | 8/1995 | Eury |
| 5,468,253 A | 11/1995 | Bezwada |
| 5,480,394 A | 1/1996 | Ishikawa |
| 5,480,794 A | 1/1996 | Peoples |
| 5,489,470 A | 2/1996 | Noda |
| 5,502,116 A | 3/1996 | Noda |
| 5,502,158 A | 3/1996 | Sinclair |
| 5,512,669 A | 4/1996 | Peoples |
| 5,516,565 A | 5/1996 | Matsumoto |
| 5,516,883 A | 5/1996 | Hori |
| 5,534,432 A | 7/1996 | Peoples |
| 5,536,564 A | 7/1996 | Noda |
| 5,550,173 A | 8/1996 | Hammond |
| 5,551,954 A | 9/1996 | Buscemi |
| 5,563,239 A | 10/1996 | Hubbs |
| 5,584,885 A | 12/1996 | Seckel |
| 5,614,576 A | 3/1997 | Rutherford |
| 5,625,030 A | 4/1997 | Williams |
| 5,629,077 A | 5/1997 | Turnlund |
| 5,635,215 A | 6/1997 | Boschetti |
| 5,646,217 A | 7/1997 | Hammond |
| 5,648,100 A | 7/1997 | Boschetti |
| 5,670,161 A | 9/1997 | Healy |
| 5,703,160 A | 12/1997 | Dehennau |
| 5,705,187 A | 1/1998 | Unger |
| 5,709,854 A | 1/1998 | Griffith-Cima et al. |
| 5,711,933 A | 1/1998 | Bichon |
| 5,728,752 A | 3/1998 | Scopelianos |
| 5,735,863 A | 4/1998 | DellaValle |
| 5,753,364 A | 5/1998 | Rutherford |
| 5,753,708 A | 5/1998 | Koehler |
| 5,783,271 A * | 7/1998 | Nishida et al. ............... 428/35.5 |
| 5,789,536 A | 8/1998 | Liggat |
| 5,811,272 A | 9/1998 | Snell |
| 5,814,071 A | 9/1998 | McDevitt |
| 5,814,599 A | 9/1998 | Mitragotri |
| 5,824,333 A | 10/1998 | Scopelianos |
| 5,824,751 A | 10/1998 | Hori |
| 5,834,582 A | 11/1998 | Sinclair |
| 5,840,331 A | 11/1998 | VanCauter |
| 5,842,477 A | 12/1998 | Naughton |
| 5,855,619 A | 1/1999 | Caplan |
| 5,874,040 A | 2/1999 | Liggat |
| 5,876,452 A | 3/1999 | Athanasiou |
| 5,876,455 A | 3/1999 | Harwin |
| 5,879,322 A | 3/1999 | Lattin |
| 5,917,002 A | 6/1999 | Doi |
| 5,919,478 A | 7/1999 | Landrau |
| 5,935,506 A | 8/1999 | Schmitz |
| 5,990,162 A | 11/1999 | Scharf |
| 5,994,478 A | 11/1999 | Asrar |
| 6,056,970 A | 5/2000 | Greenawalt |
| 6,103,255 A | 8/2000 | Levene |
| 6,119,567 A | 9/2000 | Schindler |
| 6,162,537 A | 12/2000 | Martin |
| 6,214,387 B1 | 4/2001 | Berde |
| 6,245,537 B1 | 6/2001 | Williams |
| 6,316,262 B1 | 11/2001 | Huisman |
| 6,323,010 B1 | 11/2001 | Skraly |
| 6,454,811 B1 | 9/2002 | Sherwood |
| 6,514,515 B1 | 2/2003 | Williams |
| 6,548,569 B1 | 4/2003 | Williams |
| 6,555,123 B2 | 4/2003 | Williams |
| 6,585,994 B2 | 7/2003 | Williams |
| 6,600,010 B2 | 7/2003 | Mao |
| 6,610,764 B1 | 8/2003 | Martin |
| 6,623,748 B2 | 9/2003 | Clokie |
| 6,645,622 B2 | 11/2003 | Yamane |
| 6,656,489 B1 | 12/2003 | Mahmood |
| 6,680,046 B1 | 1/2004 | Boschetti |
| 6,770,356 B2 | 8/2004 | ODonnell |
| 6,828,357 B1 | 12/2004 | Martin |
| 6,838,493 B2 | 1/2005 | Williams et al. |
| 6,867,247 B2 | 3/2005 | Williams |
| 6,867,248 B1 | 3/2005 | Martin |
| 6,878,248 B2 | 4/2005 | Signer |
| 6,878,758 B2 | 4/2005 | Martin et al. |
| 6,905,987 B2 | 6/2005 | Node |
| 7,025,980 B1 | 4/2006 | Williams |
| 7,179,883 B2 | 2/2007 | Williams |
| 7,244,442 B2 | 7/2007 | Williams |
| 7,268,205 B2 | 9/2007 | Williams |
| 7,553,923 B2 | 6/2009 | Williams |
| 2002/0028243 A1 | 3/2002 | Masters |
| 2002/0156150 A1 | 10/2002 | Williams |
| 2002/0173558 A1 | 11/2002 | Williams |
| 2003/0091803 A1 | 5/2003 | Bond |
| 2003/0185896 A1 | 10/2003 | Buiser |
| 2003/0211131 A1 | 11/2003 | Martin |
| 2004/0220355 A1 | 11/2004 | Whitehouse |
| 2004/0234576 A1 | 11/2004 | Martin |
| 2005/0025809 A1 | 2/2005 | Hasirci |
| 2005/0107505 A1 | 5/2005 | Shinoda |
| 2005/0137678 A1 | 6/2005 | Varma |
| 2005/0267516 A1 | 12/2005 | Soleimani |
| 2006/0058470 A1 | 3/2006 | Rizk |
| 2006/0177513 A1 | 8/2006 | Martin |
| 2006/0287659 A1 | 12/2006 | Terenghi |
| 2007/0010851 A1 | 1/2007 | Chanduszko |
| 2008/0051490 A1 | 2/2008 | Williams |

FOREIGN PATENT DOCUMENTS

| | | |
|---|---|---|
| CA | 2298421 | 2/2000 |
| DE | 3937649 | 5/1991 |
| EP | 0258781 | 3/1988 |
| EP | 0344704 | 12/1989 |
| EP | 0349505 | 3/1990 |
| EP | 0423484 | 4/1991 |
| EP | 0429403 | 5/1991 |
| EP | 0432443 | 6/1991 |
| EP | 0452111 | 10/1991 |
| EP | 0507554 | 10/1992 |
| EP | 0601885 | 6/1994 |
| EP | 0628586 | 12/1994 |
| EP | 0754467 | 1/1997 |
| EP | 1130043 | 9/2001 |
| EP | 1266984 | 12/2002 |
| GB | 2166354 | 5/1986 |
| JP | 62209144 | 9/1987 |
| JP | 03187386 | 8/1991 |
| JP | 04292619 | 10/1992 |
| JP | 4326932 | 11/1992 |
| JP | 5023189 | 2/1993 |
| JP | 5194141 | 11/1993 |
| JP | 06264306 | 9/1994 |
| JP | 06336523 | 12/1994 |
| JP | 7275344 | 10/1995 |

(56) References Cited

FOREIGN PATENT DOCUMENTS

| | | |
|---|---|---|
| JP | 08089264 | 4/1996 |
| JP | 08218216 | 8/1996 |
| JP | 08257055 | 8/1996 |
| JP | 09098793 | 4/1997 |
| JP | 09507091 | 7/1997 |
| JP | 00220032 | 8/2000 |
| WO | 9218164 | 10/1992 |
| WO | 9305824 | 4/1993 |
| WO | 9320134 | 10/1993 |
| WO | 9402184 | 2/1994 |
| WO | 9406886 | 3/1994 |
| WO | 9503356 | 2/1995 |
| WO | 9517216 | 6/1995 |
| WO | 9520614 | 8/1995 |
| WO | 9520615 | 8/1995 |
| WO | 9520621 | 8/1995 |
| WO | 9523250 | 8/1995 |
| WO | 9533874 | 12/1995 |
| WO | 9600263 | 1/1996 |
| WO | 9608535 | 3/1996 |
| WO | 9618420 | 6/1996 |
| WO | 9621427 | 7/1996 |
| WO | 9640304 | 12/1996 |
| WO | 9704036 | 2/1997 |
| WO | 9707153 | 2/1997 |
| WO | 9715681 | 5/1997 |
| WO | 9730042 | 8/1997 |
| WO | 9804292 | 2/1998 |
| WO | 9839453 | 9/1998 |
| WO | 9848028 | 10/1998 |
| WO | 9851812 | 11/1998 |
| WO | 9911196 | 3/1999 |
| WO | 9914313 | 3/1999 |
| WO | 9932536 | 7/1999 |
| WO | 9935192 | 7/1999 |
| WO | 0051662 | 9/2000 |
| WO | 0056376 | 9/2000 |
| WO | 0110421 | 2/2001 |
| WO | 0115671 | 3/2001 |
| WO | 0119361 | 3/2001 |
| WO | 0119422 | 3/2001 |
| WO | 02085983 | 10/2002 |
| WO | 2004101002 | 11/2004 |

OTHER PUBLICATIONS

Anderson, et al, 'Occurrence, Metabolism, metabolic Role, and Industrial Uses of bacterial Poiyhydroxyalkanoates', Microbiological Reviews, 54(4):450-72 (1990).
Andriamampandry, et al., 'Cloning of a rat brain succinic semialdehyde reductase involved in the synthesis of theneuromodulator yhydroxybutyrate', Biochem. J., 334:43-50 (1998).
Bailey, 'Free radical ring-opening polymerization,' J. Polym. Preprints 25:210-11 (1984).
Bailey, et al., "Synthesis of Poly-ecaprolactone via a free radical mechanism. Free radical ring-opening polymerization of 2-methylene-1,3-dioxepane", J. Polym. Sci. Polym. Chem., 20:3021-3030 (1982).
Bandiera, et al., 'Effect of sodium sulfonate groups on the ionic conductivity of a copolyester of thiodipropionic acid',Eur. Pol. J., 33:1679-1683 (1997).
Behrend, 'PHB as a bioresorbable material for intravascular stents,' American J. Cardiol. p. 45, TCT Abstracts (Oct. 1998).
Berde, et al., 'Sustained release of dibucaine from a biodegradable polymer matrix: A potential method for proloogedneural blockade', Abstracts of Scientific Papers, 1990 Annual Meeting, Amen. Soc. Anesthesiologists, 73(3A):A776,Sep. 1990.
Berger, et al., 'PHB recovery by hypochlorite digestion of non-PHB biomass', Biotechnonology Techniques, 3(4):227 232 (1989).
Blight, 'Miracles and molecules—progress in spinal cord repair.,' Nat. Neurosci 5:1051-4 (2002).
Boeree, et al., 'Development of a degradable composite for orthopaedic use: mechanical evaluation of anhydroxyapatite-polyhydroxybutyrate composite material', Biomaterials, 14(10):793-6 (1993).
Brandl, et al., 'Pseudomonas oleovorans as a source of poly(b-hydroxyalkanoates for potential applications asbiodegradable poly-esters', Appl. Environ. Microbiol., 54:1977-1982 (1988).
Braunegg, et al., 'Polyhydroxyalkanoates, biopolyesters from renewable resources: physiological and engineeringaspects,' J. Biotech. 65: 127-161 (1998).
Breuer, et al., 'Tissue Engineering Lamb Heart Valve Leaflets,' Biotechnology & Bioengineering 50:562-67 (1996).
Bruhn & Muller, 'Preparation and characterization of spray-dried Poly(DL-Lactide) Micro Spheres,' Proceed. Intern.Symp. Control. Rel. Bioact. Mater. 18:668-69 (1991).
Byrom, 'Miscellaneous Biomaterials,' in Biomaterials (D. Byrom, ed.) pp. 333-359 MacMillan Publishers: London, 1991.
Campbell & Bailey, 'Mechanical properties of suture materials in vitro and after in vivo implantation in horses,'Vet.Surg. 21(5):355-61 (1992).
Clavijo-Alvarez, et al 'Comparison of biodegradable conduits within aged rat sciatic nerve defects,' Plast ReconstrSurg. 119(6):1839-51(2007).
Colombo, et al., 'Involvement of GABA(A) and GABA(B) receptors in the mediation of discriminative stimulus effects ofgamma-hydroxybutyric acid', Physiology & Behavior, 64:293-302 (1998).
Conti, et al., 'Use of polylactic acid for the preparation of microparticulate drug delivery systems,' J. Microencapsulation9:153-166 (1992).
Cookson, 'It grows on trees,' Financial Times p. 6 (Aug. 12, 1992).
Cuebas, et al, 'Mitochondrial metabolism of 3-mercaptopropionic acid. Chemical synthesis of 3-mercaptopropionylcoenzyme A and some of its S-acyl derivatives', J. Biol. Chem., 260:7330-7336 (1985).
Damien & Parsons, 'Bone graft and bone graft substitutes: a review of current technology and applications,' J. Appl.Biomater. 2(3):187-208 (1991).
Dayton, et al., 'Use of an absorbable mesh to repair contaminated abdominal-wall wall defects' Archives of Surgery 121(8): 954-960 (1986).
De Groot, 'Meniscal tissue regeneration in porous 50150 copoly(L-lactide/epsiloncaprolactone) implants', Biomaterials,18(8):613-622 (1997).
De Koning, et al., 'A biodegradable rubber by crosslinking poly (hydroxyalkanoate) from Pseudomonas oleovorans',Polymer, 35:2090-97 (1994).
De Smet, et al., 'Characterization of intracellular inclusions formed by Pseudomonas oleovorans duringgrowth on octane,' J. Bacteriol., 154: 870-78 (1983).
Definition of "Region" from dictionary.com, accessed Nov. 15, 2010.
Dubois, et al., 'Macromolecular engineering of polylactones and polylactides. 12. Study of thedepolymerization reactions of poly(e-caprolactone) with functional aluminum alkoxide end groups,' Macromolecules, 26: 4407-4412 (1963).
Duvernoy, et al., 'A biodegradable patch used as a pericardial substitute after cardiac surgery: 6- and 24-month evaluation with CT', Thorac. Cardiovasc. Surg., 43(5):271-74 (1995).
Entholzner, et al., 'EEG changes during sedation with gamma-hydroxybutyric acid', Anaesthesist, 44:345-350(1995).
Ferreira, et al., "Films of Poly (L-Lactic Acid) /Poly(Hydroxybutyrate-co-Hydroxyvalerate) Blends:In vitro Degradation", Materials Research, 4(1):34-42 (2001).
Fraser, et al., 'Controlled release of a GnRH agonist from a polyhydroxybutyric acid implant-reversible suppression of themenstrual cycle in the macaque', Acta Endocrinol, 121:841-848 (1989).
Freed, et al., 'Biodegradable polymer scaffolds for tissue engineering', Biotechnology, 12:689-693 (1994).
Fuchtenbusch, et al., 'Biosynthesis of novel copolyesters containing 3-hydroxypivalic acid by Rhodoccus tuberNCIMB 40126 and related bacteria', FEMS Microbiol. Left., 159:85-92 (1998).
Fukuzaki, et al., 'Direct copolymerization of L-lactic acid with y-butyrolactone in the absence of catalysts,' DieMadromoleculare Chemie 190:1553-59 (1989).

(56) References Cited

OTHER PUBLICATIONS

Gabbay, et al., 'New outlook on pericardial substitution after open heart operations', Ann. Thorac. Surg., 48(6):803-12(1989).
Gagnon, et al., 'A thermoplastic elastomer produced by the bacterium *Pseudomonas oleovarans*', Rubber World, 207:32-38 (1992).
Gagnon, et al., 'Chemical modification of bacterial elastomers: 1. Peroxide crosslinking,' Polymer 35:4358-67 (1994).
Gerngross & Martin, 'Enzyme-catalyzed synthesis of poly[(R)-(+3-hydroxybutyrate]: formation of macroscopicgranules in vitro,' Proc. Natl. Acad. Sci. USA 92:6279-83 (1995).
Gerra, et al., 'Flumazenil effects on growth hormone response to gammahydroxybutyric acid', International ClinicalPsychopharmacology, 9:211-215 (1994).
Gordeyev, et al., "Processing of gel-spun poly($^2$-hydroxybutyrate) fibers", Journal of Applied Polymer Science, 81:2260-2264 (2001).
Griebel, et al., 'Metabolism of poly-beta-hyclroxybutyrate. I. Purification, composition, and properties of native poly-beta-hydroxybutyrate granules from *Bacillus megaterium*', Biochemistry, 7:3676-3681 (1968).
Gross, et al., 'Polymerization off/-monosubstituted-O-propiolactones using trialkylaluminum-watercatalytic systems and polymer characterization,' Macromolecules, 21: 2657-2668 (1988).
Gruber and O'Brien, "Biopolymers: Polyesters, III" (Doi, Y. and SteinbOchel, A., Eds.) Weinhelm: Wiley-VCI-1.] 4:235-250(2002).
Gugala, et al., Regeneration of segmental diaphyseal defects in sheep tibiae using resorbable polymeric membranes: apreliminary study, J. Otthop. Trauma. 13(3):187-95 (1999).
Gursel,.et al., 'In vivo application of biodegradable controlled antibiotic release systems for the treatmentof implant-related osteomyelitis,' Biornaterials 22: 73-80 (2001).
Hadlock, et al., 'Ocular cell monolayers cultured on biodegradable substrates,' Tissue Eng. 5(3):187-96 (1999).
Hazari, et a/., 'A new resorbable wrap-around implant as an alternative nerve repair technique', J. Hand Surgery, 24(3):291-295 (1999).
Hazari, et al., 'A resorbable nerve conduit as an alternative to nerve autograft in nerve gap repair', Br J Plast Surg.,52(8):653-7 (1999).
Hein, et al., 'Biosynthesis of poly(4-hydroxybutyric acid) by recombinant strains of *Escherichia coli*,' FEMS Microbiol.Lett. 153:411-18 (1997).
Heydorn, et al., 'A new look at pericardial substitutes,' J. Thorac. Cardiovasc. Surg. 94:291-96 (1987).
Hocking and Marchessault, 'Syndiotactic poly[(R,S)-0-hydroxybutyrate] isolated frommethylaluminoxane-catalyzed polymerization,' Polym. Bull., 30: 163-170 (1993).
Hocking and Marchessault, Chemistry and Technology of Biodegradable Polymers, inBiopolyesters (G.J.L. Griffin, Ed.), Chapman and Hall, London, pp. 48-96 (1988).
Hoke, 'Mechanisms of Disease: what factors limit the success of peripheral nerve regeneration in humans?' Nat. Clin.Pract. NeuroL 448-454 (2006).
Holmes, Biologically Produced (R)-3-hydroxyalkanoate Polymers and Copolymers, in Developments in Crystalline Polymers (D.C. Bassett Ed.), Elsevier, London, vol. 2, pp. 1-65 (1988).
Holmes, et al., 'Applications of PHBa microbially produced biodegradable thermoplastic,' Phys Technol 16:32-36(1985).
Hori, et al., 'Chemical synthesis of high molecular weight poly(3-hydroxybutyrate-co-4-hydroxybutyrate)' Polymer 36(24): 4703-4705 (1995).
Hori, et al., 'Ring-opening copolymerization of optically active 0-butyrolactone with several lactonescatalyzed by distannoxane complexes: synthesis of new biodegradable polyesters,' Macromolecules, 26:4388-4390 (1993).
Hori, et al., 'Ring-Opening Polymerization of Optically Active R-Butyrolactone Using Distannoxane Catalysts: Synthesis of HighMolecular Wright Poly(3-hydroxybutyrate)', Macromolecules, 26:5533-34 (1993).
Horowitz, et al., 'Novel Thermal Route to an Amorphous, Film-Forming Polymer Latex', Macromolecules, 32:3347 3352 (1999).
Horsch, 'Inheritance of Functional Foreign Genes in Plants', Science, 223 (4635):496-498 (1984).

Huijberts, et al., '*Pseudomonas putida* KT2442 cultivated on glucose accumulates poly(3-hydroxyalkanoates)consisting of saturated and unsaturated monomers', Appl Environ Microbiot, 58(2):536-44 (1992).
Hutmacher, et al., 'A review of material properties of biodegradable and bioresorbable polymers and devices for GTRand GBR applications,' Int. J. Oral Maxillofac. Implants 11(5):667-78 (1996).
Kameyama, et al., 'Novel sequence-ordered polymers by transformation of polymer backbone: Quantitative andregiosetective insertion of Thiranes into poly( S-aryl thioester)', Macromot, 32:1407-1412 (1999).
Kassab, 'Rifampicin carrying polyhydroxybutyrate microspheres as a potential chemoembolization agent', Journal of Biomaterials Science, Polymer Edition, 8(12):947-961 (1997).
Kassab, et al., 'Embolization with polyhydroxybutyrate (PHB) microspheres: In vivo studies', J. Bioact. Compat. Polym.,14:291-303 (1999).
Kaufman and Nelson, 'An overview of gamma-hydroxybutyrate catabolism: the role of the cytosolic NADP(+) dependent oxidoreductase EC 1.1.1.19 and of a mitochondrial hydroxyacid-oxoacid transhydrogenase in the initial, rate limiting step in this pathway', Neurochemical Research, 16;965-974 (1991).
Keeler, "Don\t Let Food Go to Waste—Make Plastic Out of It", R&D Magazine, 52-57 (1991).
Keeler, "Plastics Grown in Bacteria Inch Toward the Market", R&D Magazine, 46-52 (1991).
Kemnitzer, et al., "Preparation of predominantly Syndiotactic Poly(β-hydroxybutyrate) by the Tributylin Methoxide Catalyzed Ring-Opening Polymerization of racemic β-Butyrolactone", Macromolecules, 26:1221-1229 (1993).
Kim and Mooney, "Engineering smooth muscle tissue with a predefined structure", J. Biomed. Mat. Res., 41(2):322-332 (1998).
Kishida, et al., "Formulation assisted biodegradeable polymer matrices", Chemical and Pharmaceutical Bulletin, JP Pharm Society of Japan., 37(7):1954-1956(1989).
Kleinschmidt, et al., "Continuous sedation during spinal anaesthesia: gamma-hydroxybutyrate vs. propofol", European Journal of Anaesthesiology, 16:23-30 (1999).
Kleinschmidt, et al., "Total intravenous anaesthesia using propofol, gamma-hydroxybutyrate or midazolam in combination with sufentanil for patients undergoing coronary artery bypass surgery", European Journal of Anesthesiology, 14:590-599 (1997).
Klinge, et al., "Functional assessment and tissue response of short- and long-term term absorbable surgical meshes", Biomaterials, 22:1415-1424 (2001).
Koosha, et al., "Polyhydroxybutyrate as a drug carrier", Crit. Rev. Ther. Drug Carrier Syst., 6(2):117-130 (1989).
Koosha, "Preparation and characterization of biodegradable polymeric drug carriers", Ph.D. Dissertation, 1989, Univ. Nottingham, UK., Diss. Abstr. Int. B 51:1206 (1990).
Korkusuz, et al., "In vivo response to biodegradable controlled antibiotic release systems", J. Biomed. Mater. Res., 55:217-228 (2001).
Korsatko, et al., 'The influence of the molecular weight of poly-D(−)-3-hydroxybutyric acid on its use as a retard matrixfor sustained drug release,' 8th Europ. Congress of Biophannaceutics and Pharmokinetics 1:234-242 (1987).
Korte & Gelt, 'Hochdruckreaktionen. II. Die Polymerisation Von y butyrolacton and 6-valerolactam bei hohendriicken,' Polymer Lett. 4:685-89 (1966).
Kusaka, et al., 'Microbial synthesis and Physical Properties of ultra-high-molecular-weight poly((R)-3-hydroxybutyrate]', PureAppl. Chem., A35:319-35 (1998).
Lafferty, et al., 'Microbial Production of Poly-b-hydroxvbutvric acid' in Biotechnolooy (H.J. Rehm and G. Reed, eds.), Verlagsgesellschaft, Weinheim, vol. 66, pp. 135-76 (1988).
Le Borgne and Spassky, 'Stereoelective polymerization of (3-butyrolactone,' Polymer, 30: 2312-2319(1989).
Lebedev and Yevstropov, 'Thermoplastic properties of palylactones', Makromol. Chem., 185:1235-1253 (1984).
Lee, et al., 'Copolymerization of y-butyrolactone and II-butyrolactone', Macromol. Chem. Phys., 198:1109-1120 (1997).

(56) References Cited

OTHER PUBLICATIONS

Lemoigne & Roukhelman, 'Fermetation 6-Hydroxybutyrique Caracterisation et Evolution Des Produits deDeshydration et de Polymerisation de L'acide 11-Dehydroxybutyrique,' Annales des fermentations, 5:527-36 (1925).
Ljungberg, et al. 'Neuronal survival using a resorhable synthetic conduit as an alternative to primary nerve repair',Microsurgery, 19(6):259-264 (1999).
Lloyd, et al., 'Transformation of *Arabidopsis thalania* with *Agrobacterium tumefaciens*,' Science 234: 464-66 (1986).
Lutke-Eversloh et al., 'Identification of a new class of biopolymer: Bacterial synthesis of a sulfur-containing polymer withthioester linkages', Microbiology, 147(1): 11-19 (2001).
Lutke-Eversloh et al., 'List of submitted abstracts', The 8th International Symposium on Biological Polyesters,(2000).
Madison & Huisman, 'Metabolic engineering of poly(3-hydroxyalkanoates): from DNA to plastic,' Microbiol. Molec.Biol. Rev. 63:21-53 (1999).
Malm, et al., 'A new biodegradable patch for closure of atrial septal defect. An experimental study,' Scand. J. Thorac.Cardiovasc. Surg. 26(1):9-14 (1992).
Malm, et al., 'Enlargement of the right ventricular outflow tract and the pulmonary artery with a new biodegradable patchin transannular position,' Eur. Surg. Res. 26(5):298-308 (1994).
Malm, et al., 'Prevention of postoperative pericardial adhesions by closure of the pericardium with absorbable polymerpatches. An experimental study,' J. Thorac. Cardiovasc. Surg. 104(3):600-07 (1992).
Martin and Williams, 'Medical application of poly-4-hydroxybutyrate: A strong flexible absorbablebiomaterial', Biochem. Eng. J., 16:97-105 (2003).
Mathiowitz & Langer, 'Polyanhydride microspheres as drug delivery systems' in Microcapsules Nanopart. Med. Pharm. (Donbrow, ed.), pp. 99-123 (CRC:Boca Raton, Florida, 1992).
Maysinger, et al., 'Microencapsulation and the Grafting of Genetically Transformed Cells as Therapeutic Strategies torescue Degenerating Neurons of the CNS,' Reviews in the Neurosciences, 6:15-33 (1995).
McMillin, et al., 'Elastomers for Biomedical Applications,' Rubber Chemistry and Technology 67:417-446 (1994).
McWilliams, 'Plastics as High as an Elephant's Eye?' Business Week, pp. 110-111 (1991).
Modelli, et al., 'Kinetics of aerobic polymer degradation in soil by means of the ASTM D 5988-96 standard method,' JEnviron Polym Degr 7:109-116 (1999).
Muh, et al., 'PHA synthase from chromatium vinosum: cysteine 149 is involved in covalent catalysis', Bioche., 38:826 837 (1999).
Muller, et al., 'Poly(hydroxyalkanoates): A Fifth Class of Physiologically Important Organic Biopolymers,' Angew.Chem. int. Ed. Engl. 32:477-502 (1993).
Nakamura, et al., 'Microbial synthesis and characterization of poly(3-hydroxybutyrate-co-4-hydroxybutyrate),' Macromol. 25:4237-41 (1992).
Nakamura et al., 'Biosynthesis and characteristics of bacterial poly(3-hydroxybutyrate-co-3-hydroxypropionate)',Macromol. Rep., A28, 15-24 (1991).
Nelson, et al., 'The extraneural distribution of gamma-hydroxybutyrate', J. Neurochem., 37:1345-1348 (1981).
Niklason, et al., 'Functional arteries grown in vitro,' Science 284(5413):489-93 (1999).
Nobes, et al., 'Polyhydroxyalkanoates: Materials for delivery systems,' Drug Del. 5:167-77 (1998).
Ogawa, et al., 'A New Technique to Efficiently Entrap Leuprolide Acetate into Microcapsules of Poly Lactic Acid orCopoly(Lactic/ Glycolic) Acid,' Chem. Pharm. Bull. 36:1095-103 (1988).
Otera, et al., 'Distannoxane-catalysed transesterification of 1,n-Dioldiacetates. Selective transformation of either ofchemically equivalent functional groups,' J. Chem. Soc. Chem. Commun. 1742-43 (1991).
Otera, et al., 'Distannoxane as reverse micelle-type catalyst: novel solvent effect on reaction rate of transesterification,' J. Org. Chem. 54:4013-14 (1989).
Otera, et al., 'Novel distannoxane-catalyzed transesterification and a new entry to 0,3-unsaturated carboxylic acids,' Tetrahedron Lett., 27:2383-86 (1986).
Otera, et al., 'Novel template effects of distannoxanne catalysts in highly efficient transesterification and esterification,' J. Org. Chem. 56:5307-11 (1991).
Pedros-Alio et al., 'The influence of poly-3-hydroxybutyrate accumulation on cell volume and buoyant density in*Alcaligenes eutrophus*', Arch. Microbiol. 143:178-184 (1985).
Peoples, et al., 'Poly-3-hydroxybutyrate Biosynthesis in *Alcaligenes eutrophus* H16,' J. Biol. Chem 264(26):15293-97(1989).
Peoples, et al., 'Polyhydroxybutyrate (PHB): A Model System for Biopolymer Engineering: II,' in Novel Biodegradable Microbial Polymers (Dawes, ed.) pp. 191-202, Kluwer Academic Publishers:Netherlands (1990).
Perrin & English, 'Polycaprolactone,' in Handbook of Bioabsorbable Polymers (Dumb, et al., eds.) pp. 63-77 (Harwood, Amsterdam, 1997).
Pinto, 'Hydrogen Peroxide as depyrogenation agent for medical devices components', Revista De Saude Publica,29(1):75-79 (1995).
Poirier, 'Perspectives on the production of polyhydroxyalkanoates in plants,' FEMS Microbiology Reviews 103:237-46(1992).
Poirier, et al., 'Progress Toward Biologically Produced Biodegradable thermoplastics,' Adv. Mater. 5(1):30-37 (1993).
Pool, 'In Search of the Plastic Potato,' Science 245: 1187-89 (1989).
Pouton & Akhtar, 'Biosynthetic polyhydroxyalkanoates and their potential in drug delivery,' Adv. Drug Delivery Rev.18:133-62 (1996).
Rehm and Steinbuchel, 'Biochemical and genetic analysis of PHA synthases and other proteins required for PHAsynthesis', Int. J. Biol. Macromol. 25:3-19 (1999).
Renstad, et al., 'The influence of processing induced differences in molecular structure on the biological and non biological degradation of poly(3-hydroxybutyrate-co-3-hydroxyvalerate), P(3-HB-co-3-HV),' Polymer Degradation andStability 63:201-211 (1999).
Reynolds, Martindale: The Extra Pharmacopeia, p. 1264, (Thirty First Edition, Royal Pharmaceutical Society, London, 1997).
Rivard, et al., 'Fibroblast seeding and culture in biodegradable porous substrates,' J. Apt Biomater. 6(1):65-68(1995).
Ropero-Miller & Goldberger, 'Recreational drugs. Current trends in the 90s', Clinics in Laboratory Medicine,18:727-746 (1998).
Sabbagh, et al., '3-Mercaptopropionic acid, a potent inhibitor of fatty acid oxidation in rat heart mitochondria', J. Biol.Chem. 260:7337-7342 (1985).
Saito, et al., 'Microbial synthesis and properties of poly(3-hydroxybutyrate-co-4-hydroxybutyrate) in Comamonasacidovorans,' Int. J. Biol. Macromol. 16(2):99-104 (1994).
Scharf, et al, 'Pharmacokinetics of gammahydroxybutyrate (GHB) in narcoleptic patients', Sleep 21:507-514 (1998).
Schlegel, et al., 'Ein submersverfahren zur kultur wasserstoffoxydierender bakterien: Wachstumsphysiologischeuntersuchungen', Arch. Mikrobiol. 38:209-222 (1961).
Schlosshauer, 'Synthetic nerve guide implants in humans: a comprehensive survey.' Neurosurgery 59:740-748(2006).
Schmidt, et al 'Neural tissue engineering: strategies for repair and regeneration,' Annu. Rev. Biomed. Eng. 5:293-347(2003).
Sendelbeck & Girdis, 'Disposition of a 14C-labeled bioerodible polyorthoester and its hydrolysis products, 4-hydroxybutyrate and cis,trans-1,4-bis(hydroxymethyl)cyclohexane, in rats', Drug Metabolism & Disposition 13:291-295(1985).
Shinoka, et al., 'Creation of viable pulmonary artery autografts through tissue engineering,' J. Thorac. Cardiovasc.Surg. 115(3):536-46 (1998).
Shinoka, et al., 'Tissue engineering heart valves: valve leaflet replacement study in a lamb model' Ann. Thorac. Surg.60(6 Suppl):S513-16 (1995).

(56) References Cited

OTHER PUBLICATIONS

Shinoka & Mayer, 'New frontiers in tissue engineering: tissue engineered heart valves' in Synthetic Bioabsorbable Polymer Scaffolds (Atala & Mooney, eds.) pp. 187-198 Birkhaiser Boston, 1997.
Sim, et al., 'PHA synthase activity controls the molecular weight and polydispersity of polyhydroxybutyrate in vivo,' Nat.Biotechnol. 15(1):63-67 (1997).
Skrede et al, 'Thia fatty acids, metabolism and metabolic effects' in Biochim Biophys Acta 1344:115-31 (1997).
Snead, 'The gamma-hydroxybutyrate model of absence seizures: correlation of regional brain levels of gamma hydroxybutyric acid and gamma-butyrolactone with spike wave discharges', Neuropharmacology 30:161-167 (1991).
Song, et al., 'Production of poly(4-hydroxybutyric acid) by fed-batch cultures of recombinant strains of *Escherichia coli*',BiotechnoL Lett. 21:193-197 (1999).
Speer & Warren, 'Arthroscopic shoulder stabilization. A role for biodegradable materials,' Clin. Otthop. (291):67-74(1993).
Stanton & Gagne, 'The remarkable catalytic activity of alkali-metal alkoxide clusters in the ester interchangereaction,' J. Am. Chem. Soc. 119:5075-76 (1997).
Steinbuchel, 'Molecular basis for biosynthesis and accumulation of polyhydroxyalkanoic acids in bacteria,' FEMSMicrobial. Rev. 103:217-230 (1992).
Steinbuchel, 'Polyhydroxyalkanoic Acids' in Biomaterials (Byrom, ed.), pp. 125-213 (MacMillan Publishers:London 1991).
Steinbuchel, et al. 'Diversity of Bacterial Polyhydroxyalkanoic Acids', FEMS Microbial. Lett. 128:219-228 (1995).
Steinbuchel & Wiese, 'A *Pseudomonas* strain accumulating polyesters of 3-hydroxybutyric acid and medium-chain length 3-hydroxyalkanoic acids,' Appl. Microbiol. Biotechnol. 37:691-97 (1992).
Takagi et al., 'Biosynthesis of polyhydroxyalkanoate with a thiophenoxy side group obtained from *Pseudomonasputida*', Macromolecules, 32: 8315-8318 (1999).
Talja, et al., 'Bioabsorbable and biodegradable stents in urology,' J. Endourol. 11(6):391-97 (1997).
Tanahashi, et al., 'Thermal Properties and Stereoregularity of Poly(3-hydroxybutyrate) Prepared from optically Activefl-Butyrolactone with a Zinc-Based Catalyst,' Macromolecules 24:5732-33 (1991).
Tanaka, et al., 'Clinical application of 4-hydroxybutyrate sodium and 4-butyrolactone in neuropsychiatric patients', PallePsychiatrica et Neurologica 20:9-17 (1966).
Tanguay, et al., 'Current status of biodegradable stents,' Cardiol. Clin. 12 (4):699-713 (1994).
Tepha announces submission of device master file to FDA (Jun. 3, 2002), Retrieved Dec. 17, 2004, from http://www.pressrelease.be/script UK/newsdetail.asp?ndavs=m&ID=695.
Tepha submits device master file to FDA—New Technology (Jul. 2, 2002). Retrieved on Dec. 17, 2004, from http://www.findarticles.eom/p/articles/mi mOPC/is7 26/ai 89018276.
Tunnicliff, 'Sites of action of gamma-hydroxybutyrate (GHB)—a neuroactive drug with abuse potential', ClinicalToxicology, 35:581-590 (1997).
Turesin, et al., 'Biodegradable polyhydroxyalkanoate implants for osteomyelitis therapy: in vitro antibiotic release,' J. Biomaier. Sci. Polymer Edn. 12:195-207 (2001).
Turke, 'Absorbable Biomaterial is suited for diverse applications' (Jun. 3, 2002). Retrieved on Dec. 17, 2004, from http://www.devicelink.eom/mpmn/archive/01/10/009.html.

Unverdorben, et al., 'Polyhydroxybutyrate (PHB) Biodegradable Sient-Experience Experience in the Rabbit,' American J. Cardiol, p. 46, TCT Abstracts (Oct. 1998).
Valappil, et al., 'Biomedical applications of polyhydroxyalkanoates, an overview of animal testing and in vivo responses', Expert Rev. Med. Devices, 3(6):853-868 (2006).
Valentin, et al, Identification of 4-hydroxyhexanoic acid as a new constituent of biosynthetic polyhydroxyalkanoic acids from bacteria, Appl. Microbiol. Biotechnol, 40:710-16 (1994).
Valentin, et al., 'Identification of 5-hydroxyhexanoic acid, 4-hydroxyaheptanoic acid and 4-hydroxyoctanoic acid as new constituents of bacterial polyhydroxyalkanoic acids', Appl. Microbiol. Biotechnol., 46:261-67 (1996).
Valentin, et al., 'Production of poly(3-hydroxybutyrate-co-4-hydroxybutyrate) in recombinant *Escherichia coli* grown on glucose,' J. Biotechnol. 58:33-38 (1997).
Von Schroeder, et al., 'The use of polylactic acid matrix and periosteal grafts for the reconstruction of rabbit knee articular defects', J. Biomed. Mater. Res., 25(3):329-39 (1991).
Wallen & Rohwedder, "Poly-b-hydroxyalkanaate tram activated sludge", Environ. Sci. TechnoL, 8:576-579 (1974).
Widmer & Mikos. 'Fabrication of biodearadable polvmer scaffolds for tissue enaineersna' in Frontiers in Tissue Engineering (Patrick, etal., Eds.) Ch, II.5, pp. 107-120 (Elsevier Science, NewYork, 1998).
Williams, et al., 'Application of PHAs in Medicine and Pharmacy', Polyesters III, 4:91-127 (2002).
Williams, et al., 'PHA applications: addressing the price performance issue. I. Tissue engineering,' Int. J. Biol.Macromol. 25(1-3): 111-121 (1999).
Williams & Peoples, 'Biodegradable plastics from plants,' CHEMTECH 26:38-44 (1996).
Williams & Peoples, 'Making plastics green,' Chem. Br. 33#3A)2D#32 (1997).
Wodzinska, et al., 'Polyhydroxybutyrate synthase: Evidence for covalent catalysis', J. Am. Chem. Soc. 118:6319-6320(1996).
Wong & Mooney, 'Synthesis and properties of biodegradable polymers used as synthetic matrices for tissue engineering', in Synthetic Biodegradable Polymer Scaffolds (Atala, et at., eds.) DP. 51-82 (Birkhauser: Boston, 1997).
Worsey and Williams, 'Metabolism of toluene and xylenes by *Pseudomonas putida* (arvilla) mt-2: evidence for a new function of the TOL plasmid' J Bacteriol 124:7-13 (1975).
Xie, et al., 'Ring-opening Polymerization of a-Butyrolactone by Thermophilic Lipases,' Macromolecules 30:6997-98(1997).
Yagmurlu, et al,, 'Sulbactam-cefoperazone polyhydroxybutyrate-co-hydroxyvalerate (PHBV) local antibiotic delivery system: in vivo effectiveness and biocompatibility in the treatment of implant-related experimental osteomyelitis', J Biomed Mater Res., 46(4):494-503 (1999).
Yamada, et al., 'Development of a dura! substitute from synthetic bioabsorbable polymers', J. Neurosurg., 86(6)1012-17(1997).
Yiu, et al. 'Glial inhibition of CNS axon regeneration,' Nat. Rev. Neurosci, 7:617-627 (2006).
Zund, et al., 'The in vitro construction of a tissue engineered bioprosthetic heart valve,' Eur. J. Cardiothorac. Surg.11(3):493-97 (1997).
Gursel, et al., "In vitro antibiotic release from poly(3-hydroxybutyrate-co-3-hydroxyvalerate) rods", Microencapsulation, 19(2):153-64 (2002).

* cited by examiner

MEDICAL DEVICES CONTAINING ORIENTED FILMS OF POLY-4-HYDROXYBUTYRATE AND COPOLYMERS

RELATED APPLICATIONS

This application is a continuation of pending prior application U.S. Ser. No. 11/931,850 filed Oct. 31, 2007, now U.S. Pat. No. 7,943,683, entitled "Medical Devices Containing Oriented Films of Poly-4-Hydroxybutyrate and Copolymers", by Said Rizk, David P. Martin, Kicherl Ho, and Simon F. Williams, which claims priority under 35 U.S.C. 119 to U.S. Ser. No. 60/868,182 filed Dec. 1, 2006, both of which are herein incorporated by reference in their entirety.

FIELD OF THE INVENTION

The present invention generally relates to polymeric compositions that can be processed into films using continuous processes to produce products having substantially uniform physical properties, including physical and thermo-mechanical integrity. The compositions include polymers or copolymers comprising 4-hydroxybutyrate, and can be processed into films that are tough, have high strength and low modulus.

BACKGROUND OF THE INVENTION

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Cambridge, Mass.). Poly-4-hydroxybutyrate (P4HB, TephaFLEX® biomaterial) is a strong, pliable thermoplastic polyester that, despite its biosynthetic route, has a relatively simple structure

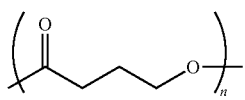

The polymer belongs to a larger class of materials called polyhydroxyalkanoates (PHAs) that are produced by numerous microorganisms (see, for example: Steinbüchel A., et al. Diversity of Bacterial Polyhydroxyalkanoic Acids, *FEMS Microbial. Lett.* 128:219-228 (1995)). In nature these polyesters are produced as storage granules inside cells, and serve to regulate energy metabolism. They are also of commercial interest because of their thermoplastic properties, and relative ease of production. Several biosynthetic routes are currently known to produce P4HB:

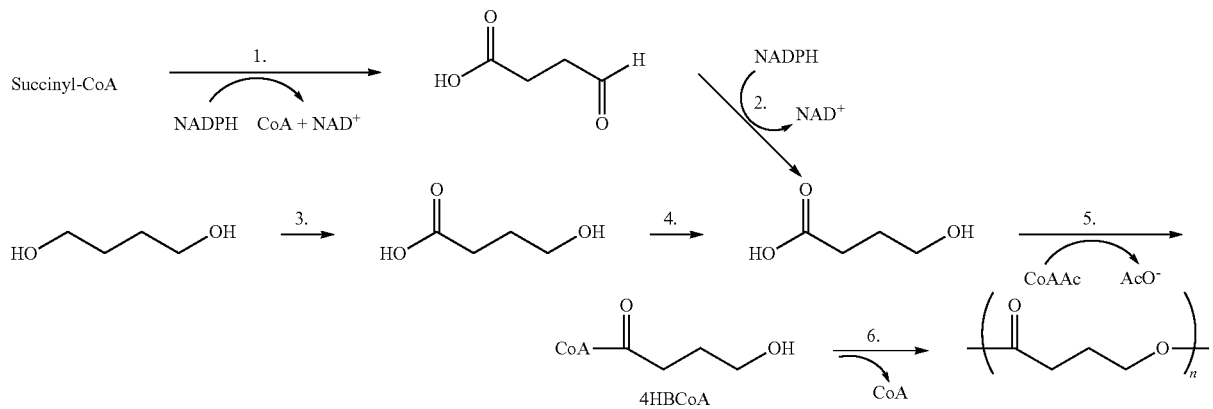

This schematic shows some of the known biosynthetic pathways for the production of P4HB. Pathway enzymes are: 1. Succinic semialdehyde dehydrogenase, 2. 4-hydroxybutyrate dehydrogenase, 3. diol oxidoreductase, 4. aldehyde dehydrogenase, 5. Coenzyme A transferase and 6. PHA synthetase.

Chemical synthesis of P4HB has been attempted, but it has been impossible to produce the polymer with a sufficiently high molecular weight that is necessary for most applications (Hori, Y., et al., *Polymer* 36:4703-4705 (1995)).

U.S. Pat. Nos. 6,245,537, 6,623,748 and 7,244,442 describe methods of making PHAs with little to no endotoxin, which is suitable for medical applications. U.S. Pat. Nos. 6,548,569, 6,838,493, 6,867,247, 7,268,205, and 7,179,883 describe use of PHAs to make medical devices. Copolymers of P4HB include 4-hydroxybutyrate copolymerized with 3-hydroxybutyrate or glycolic acid (U.S. patent application No. 20030211131 by Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III,* 4:91-127 (2002), and by Martin, D. et al. Medical Applications of Poly-4-hydroxybutyrate: A Strong Flexible Absorbable Biomaterial, *Biochem. Eng. J.* 16:97-105 (2003). Medical devices and applications of P4HB have also been disclosed by WO 00/56376 to Williams et al.

Several patents including U.S. Pat. Nos. 6,555,123, 6,585,994, and 7,025,980 describe the use of PHAs in tissue repair and engineering.

In the practice of surgery there currently exists a need for absorbable films with improved performance. These films can be used, for example, to reinforce tissue structures. They may also be used as anti-adhesion membranes, or as components of other devices. A number of other absorbable materials have been used to produce films for use in surgery. For example, films have been made from polylactic acid (PLA) or copolymers containing the different stereoisomers of lactic acid or glycolic acid. SurgiWrap™, for example, is a medical film implant made from a copolymer of L-lactide and D,L-lactide, 70:30. These materials do not, however, have ideal properties for many procedures and applications. Films made from PLA, like SurgiWrap™, have high modulus values, making them stiff, and preventing these films from contouring to bodily tissues when implanted. The high modulus values of PLA [see Gruber and O'Brien, 2002, in Biopolymers: Polyesters, III (Doi, Y. and Steinbüchel, A., Eds.) vol. 4, pp. 235-250. Weinheim: Wiley-VCH.] result in films of low toughness, and these properties, combined with other PLA properties, limit the ability of the polymer scientist to process PLA into thin films with good handling properties, for example, by solvent casting and melt extrusion.

U.S. Pat. No. 6,548,569 to Williams et al. discloses an unoriented film of poly-4-hydroxybutyrate produced by compression molding in a batch process, not a continuous process. The film had a tensile strength of 5.27 kgf/mm$^2$ (7,500 psi), tensile modulus of 6.6 kgf/mm$^2$ (9,400 psi), and elongation at break of 1,000%.

It is an object of the present invention to provide methods to produce films of absorbable polymers that have relatively low modulus values, and which are tough and have high strength.

It is a further object of the present invention to provide continuous processes to produce such films, such as melt processing and solvent casting, as compared to batch processes such as compression molding.

It is another object of the present invention to provide films which can be used in medical applications, for example, as implants such as devices for anti-adhesion barriers, tissue separation and temporary tissue support, coatings on medical devices, including stent coatings, as well as devices for tissue in-growth particularly where the film has been rendered porous.

It is therefore an object of the invention to provide continuous processes for polymer film production which yield materials with excellent physical and mechanical properties, and the resulting polymer films.

SUMMARY OF THE INVENTION

Continuous processing methods for making absorbable polymeric films with one or more of the following properties: high toughness, low modulus, high tensile strength, and thickness less than 10 mm, more preferably less than 1 mm, and more preferably less than 100 µm, have been developed. In the preferred embodiment, the polymer is a polyhydroxyalkanoate, and in the most preferred embodiment, the polymer comprises 4-hydroxybutyrate. A particularly preferred embodiment is a film of poly-4-hydroxybutyrate or copolymer thereof, wherein the film has a tensile strength greater than 5.5 kgf/mm$^2$, tensile modulus less than 181 kgf/mm$^2$, and elongation at break from 10-500%, wherein the film is derived by a continuous process such as melt extrusion or solvent casting, followed by orientation to more than 25% of the film's original length in one or more directions.

These can be used for a variety of purposes including fabrication of medical devices.

DETAILED DESCRIPTION OF THE INVENTION

Definitions

"Poly-4-hydroxybutyrate" as generally used herein means a homopolymer comprising 4-hydroxybutyrate units. It may be referred to herein as P4HB or TephaFLEX® biomaterial (manufactured by Tepha, Inc., Cambridge, Mass.).

"Copolymers of poly-4-hydroxybutyrate" as generally used herein means any polymer comprising 4-hydroxybutyrate with one or more different hydroxy acid units.

"Blend" as generally used herein means a physical combination of different polymers, as opposed to a copolymer comprised of two or more different monomers.

Orientation is the process by which the film is stretched beyond its yield point and plastically deformed, but does not break (i.e. it retains mechanical and physical integrity). The degree of orientation may be expressed as the percentage or ratio that the film is stretch when compared to the original film prior to orientation. Films are preferably oriented by stretching the film by at least 25% of the film's original length in one or more directions.

"Tensile modulus" is the ratio of stress to strain for a given material within its proportional limit. As used herein, low tensile modulus means a material having a tensile modulus less than 180 kgf/mm$^2$.

"Tensile strength" is the maximum or ultimate tensile load per unit area of original cross section area of the test specimen, within the gauge boundaries, sustained by the specimen during the test. As used herein, high tensile strength means a material test sample having a tensile strength of at least 5.3 kgf/mm$^2$.

"Toughness" means a property of a material by virtue of which it can absorb energy; the actual work per unit volume or unit mass of material that is required to rupture it. Toughness is usually proportional to the area under the load-elongation curve such as the tensile stress-strain curve. (Rosato's Plastics Encyclopedia and Dictionary, Oxford Univ. Press, 1993.) As used herein, high toughness means a value greater than 10 kgf/mm$^2$.

"Elongation" or extensibility of a material means the amount of increase in length resulting from, as an example, the tension to break a specimen. It is expressed usually as a percentage of the original length. (Rosato's Plastics Encyclopedia and Dictionary, Oxford Univ. Press, 1993.)

"Molecular weight" as used herein, unless otherwise specified, refers to the weight average molecular weight (Mw), not number average molecular weight (Mn).

"Absorbable" as generally used herein means the material is broken down in the body and eventually eliminated from the body within five years.

"Biocompatible" as generally used herein means the biological response to the material or device being appropriate for the device's intended application in vivo. Any metabolites of these materials should also be biocompatible.

I. Composition

Methods have been developed to produce films of P4HB and copolymers with exceptional toughness. These methods may be used to prepare films that have substantially uniform physical properties and physical integrity. The methods may be run continuously, which is particularly advantageous in manufacturing. These films can be prepared by solution casting or by melt extrusion followed by orientation.

A. Polymers

The processes described herein can typically be used with any of the polyhydroxyalkanoate polymers, including blends and copolymers thereof.

In a preferred embodiment, the polymer is poly-4-hydroxybutyrate (P4HB) or a copolymer thereof. Copolymers include P4HB with 3-hydroxybutyrate, and P4HB with glycolic acid monomer. P4HB and copolymers thereof can be obtained from Tepha, Inc. of Cambridge, Mass.

B. Films

In a preferred embodiment, films can be prepared with thickness of less than 10 mm, more preferably less than 1 mm, and even more preferably less than 100 µm. It has been discovered that very thin films of P4HB polymer or copolymers thereof can be prepared with substantially uniform physical properties, and physical integrity, by solution casting. Using this method, films cast from solutions of the polymer or copolymers dissolved in organic solvents can have thicknesses that are less than 100 µm, and even less than 50 µm. For example, solution cast films of P4HB have been prepared with thicknesses of 20 to 50 µm. With appropriate choice of solvent, polymer and casting conditions, thinner films of P4HB can be produced, or the cast films can be stretched and oriented uniaxially or biaxially to yield thinner and stronger films than the unoriented cast films.

It has also been discovered that very thin films of P4HB and copolymer thereof can be prepared with exceptional toughness and strength. These cast films have a tensile strength of approximately 7.2 kgf/mm$^2$ and elongation to break of approximately 200%. In comparison, a commercially available implantable film of PLA (SurgiWrap™ Bioresorbable Film) has a tensile strength of approximately 5.9 kgf/mm$^2$ and an elongation to break of 95%.

Films of P4HB polymer or copolymers thereof, with exceptional toughness, can be prepared by melt processing followed by orientation (stretching). For example, a film of P4HB may be prepared by melt extrusion followed by stretching. Stretching substantially increases stress as measured in kgf/mm$^2$. For example, the stress in an unoriented P4HB film prepared by melt extrusion, thickness of 0.022 mm and width of 13 mm was measured on a MTS mechanical analyzer to be 4.98 kgf/mm$^2$. The stress in the same P4HB film after stretching the sample 3.6× the original length to a thickness of 0.010 mm and width of 8 mm was measured to be 14.13 kgf/mm$^2$ with an elongation to break of the oriented (or stretched) sample of approximately 25%.

Comparative ball burst testing can be done by ASTM D6797-02, [Standard Test Method for Bursting Strength of Fabrics Constant-Rate-of-Extension (CRE) Ball Burst Test (1 cm ball, 1.6 cm opening)]. This testing shows that P4HB films are stronger and tougher than SurgiWrap™ film, another commercially available, absorbable film used as an implant material. Ball burst strength and elongation for a 40 µm P4HB film were 5.6 kgf and 39 mm (ball displacement at break), respectively, while for SurgiWrap they were 3.2 kgf and 3.4 mm (ball displacement at break), respectively, for a slightly thicker film (50 µm). The higher breaking force and longer extension to break for the P4HB film demonstrate its greater strength and toughness.

In a preferred embodiment, the films described herein have toughness greater than 10 kgf/mm$^2$, more preferably greater than 50 kgf/mm$^2$, and even more preferably greater than 100 kgf/mm$^2$.

In a preferred embodiment, the films described herein preferably have tensile strength greater than 5.5 kgf/mm$^2$, more preferably greater than 7.0 kgf/mm$^2$, and even more preferably greater than 10.0 kgf/mm$^2$.

In a preferred embodiment, the films described herein preferably have an elongation to break greater than 10%, more preferably greater than 15%, and even more preferably greater than 20%.

C. Other Components

The P4HB polymer and copolymer films may contain other materials, including plasticizers, nucleants, other polymers, additives, and compatibilizers. Examples of plasticizers are disclosed by U.S. Pat. No. 6,905,987 to Noda et al. Other components may be added to impart benefits such as, but not limited to, increased stability, including oxidative stability, brightness, color, flexibility, resiliency, workability, processibility (by addition of processing aids), viscosity modifiers, and odor control.

Active components, including therapeutic, diagnostic and/or prophylactic agents, such as drugs, or other substances may be incorporated. Such compositions may be used for controlled release of the drugs or other substances. These may be proteins, peptides, sugars, polysaccharides, glycoproteins, lipids, lipoproteins, nucleic acid molecules, or combinations thereof. Moreover, the films may comprise proteins, polysaccharides, peptides, as well as other substances including allograft and xenograft materials. It may be advantageous to incorporate contrast agents, radiopaque markers, or radioactive substances.

For certain applications it may also be desirable to incorporate fillers, including materials such as titanium dioxide, calcium carbonate, hydroxyapatite, and tricalcium phosphate. Such fillers may include agents that can subsequently be leached or washed out of the film to render it porous.

D. Formation into Devices

Films made from P4HB polymers and copolymers thereof by solvent casting and melt extrusion are characterized by their thinness, which may be less than 100 µm, and even less than 50 µm. These films are also characterized by high tensile strength and toughness and high ductility prior to orientation. These films have properties that are substantially improved for medical application relative to PLA-based films.

The films possess properties that are desirable in preparing medical products, particularly implantable medical devices. For example, the films may be used to make partially or fully absorbable biocompatible medical devices, or components thereof. Such devices include, but are not limited to: stent, stent graft, stent coating, drug delivery device, device for temporary wound or tissue support, repair patch, tissue engineering scaffold, retention membrane (for example, to retain bone graft), anti-adhesion membrane, tissue separation membrane, hernia repair device, device coating (including devices to improve fixation), cardiovascular patch, catheter balloon, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, including but not limited to atrial septal defect repair devices and PFO closure devices, left atrial appendage (LAA) closure device, pericardial patch, bulking and filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

II. Methods of Manufacturing Films

A. Method of Making P4HB Polymer or Copolymer Films by Solvent Casting

In a preferred method, a film of P4HB polymer or copolymer thereof may be prepared by solution casting as follows. A homogeneous solution of P4HB in a suitable solvent such as 1,4-dioxane or tetrahydrofuran (THF) is prepared at approximately 10-15 wt/vol %. The solution should have a viscosity of approximately 400 to 7,400 cP. The polymer solution is pumped at approximately room temperature through a 150 mm slot die with a 400 µm die gap onto a moving web, for example, of aluminum foil. The web speed is approximately 0.5 m/min and traveled 5 m before being collected on a collection roller. The speed is adjusted to ensure evaporation of the solvent. One or more separate air drying zones set at 50-60° C. were employed to remove solvent from the polymer film before collection on the final roll. A number of parameters can be varied to control the film thickness including, but not limited to, the pump speed, the die gap and width, the polymer concentration and the web speed.

B. Method of Making P4HB Polymer or Copolymer Films by Melt Processing Through Melt Extrusion Films can also be prepared by melt-extrusion methods. Preferred methods are a T-die extrusion method or an inflation method.

In the formation of the film by melt-extrusion, the barrel and T-die temperatures for preferably carrying out the formation are 80 to 250° C., more preferably 100 to 210° C. The melting of the P4HB is insufficient at temperature less than 100° C. When the temperature is higher than 250° C., the P4HB markedly undergoes thermal decomposition. However, the site of the barrel directly below a hopper may have a temperature of less than 100° C. The molten film exits the T-die and is cast over a chilled moving surface preferably, one or more rotating cylindrical cast rollers with surface temperature maintained at 5-100° C., but more preferably at 10° C. This step is followed by a take-up step to wind up the extruded film. Film thickness can be varied by changing the gap of the T-die slit, polymer flow rate, and cast roll speed.

In the formation of film by the inflation method, an inflation molding circular die is used instead of a T-die to extrude cylindrical film of P4HB. The molten cylindrical film is cooled and solidified by blowing it up with cold air blown from the central portion of the circular die, and the cylindrical film which had been blown up is collected with a take-up machine. Film thickness can be varied by changing the gap of the inflation die slit, polymer flow rate, cooling air pressure and temperature and take-up speed.

C. Orientation of Films

The melt-extrusion films and solvent cast films show improved mechanical properties when stretched. The melt-extrusion film may be stretched by several methods such as a roll stretching and/or a stretching method using a tenter frame. The melt-extrusion film can be stretched at a temperature between room temperature and 150° C. at a stretch ratio of 0.25 to 15. To increase the processing rate, the stretching may be more preferably carried out at a temperature in the range of from 40 to 80° C. The stretching may be monoaxial stretching for forming a monoaxially oriented film, consecutive biaxial stretching for forming a biaxially oriented film and simultaneous biaxial stretching for forming a plane-oriented film. When the melt-extrusion film is stretched, the tensile strength at break in the direction in which the film is stretched is increased.

The present invention will be further understood by referenced to the following non-limiting examples.

Example 1

Preparation of Solvent Cast P4HB Film by a Continuous Process

A homogeneous solution of P4HB in 1,4-dioxane (15% wt/vol) was prepared by dissolving 91 g of P4HB in 610 ml of 1,4-dioxane. This solution had a viscosity of approximately 7,400 cP. The polymer solution was pumped at approximately 36 ml/min at room temperature through a 150 mm slot die with a 400 µm die gap onto a moving web of aluminum foil. The web speed was approximately 0.5 m/min and traveled 5 m before being collected on a collection roller. Three separate air drying zones set at 50-60° C. were employed to desolventize the polymer film before collection on the final roll. Using these conditions, a 43 µm thick film was obtained. A thinner film (24 µm thick) was obtained by increasing the web speed to 0.75 m/min and reducing the polymer concentration to 10%. Thinner films may also be obtained by reducing the die gap or pump speed. Mechanical properties of the solvent cast films compared to commercially available SurgiWrap™ 70:30 Poly (L-lactide-co-D,L-lactide) are shown in Tables 1 and 2.

TABLE 1

Tensile mechanical properties of solvent cast P4HB films versus SurgiWrap ™ Bioresorbable Film.

| Description | Thickness (mm) | Tensile Strength (kgf/mm$^2$) | Elongation at break (%) | Tensile Modulus (kgf/mm$^2$) |
|---|---|---|---|---|
| P4HB Solvent Cast Film | 0.043 | 7.2 | 238 | 93 |
| P4HB Solvent Cast Film | 0.024 | 5.6 | 186 | 102 |
| SurgiWrap ™ 70:30 Poly (L-lactide-co-D,L-lactide) | 0.050 | 5.0 | 95 | 181 |

TABLE 2

Ball burst properties of solvent cast P4HB film and SurgiWrap ™ Bioresorbable Film. (1.0 cm ball, 1.6 cm opening, 300 mm/min ball per ASTM D6797-2)

| Description | Thickness (mm) | Peak Load (kg) | Ball displacement at break (mm) |
|---|---|---|---|
| P4HB Solvent Cast Film | 0.040 | 5.6 | 39 |
| P4HB Solvent Cast Film | 0.024 | 4.3 | 43 |
| SurgiWrap ™ | 0.050 | 3.2 | 3.4 |

Example 2

Preparation of a P4HB Film by Extrusion Casting and Stretching

P4HB (Tepha, Inc., Cambridge, Mass.) (Mw 506,000) was ground into small pieces using a Fritsch cutting mill (Pulversette 15, 10 mm bottom sieve) and dried under vacuum overnight to less than 0.01% (w/w) water. Dried pellets of the polymer were fed into an extruder barrel of a Leistritz 27 mm, 40:1 L/D co-rotating twin screw extruder fitted with 10 inch wide coat-hanger die with adjustable die lips initially set at 0.015 inch gap. Eleven heating zones of the extruder were set at 75, 90, 110, 110, 130, 130, 130, 150, 150, 200 and 200° C. and the die temperature was set at 200° C. Polymer feed rate was set at 1 lb/hr and the extruder speed was set at 100 rpm. Melt pressure measured 247 psi and melt temperature measured 208° C. A 7-inch diameter roll was used for casting. Roll surface temperature was kept at 12° C. and film line speed was maintained at 3 feet per minute. The properties of a film derived by this process before and after biaxial orientation is shown in Table 3.

TABLE 3

Tensile mechanical properties of P4HB film produced by a melt extrusion process before and after orientation

| Specimen | Thickness (mm) | Width (mm) | Load (kgf) | Tensile Stress (kgf/mm$^2$) | Elongation at Break (%) | Tensile Modulus (kgf/mm$^2$) | Toughness (kgf/mm$^2$) |
|---|---|---|---|---|---|---|---|
| Unoriented | 0.035 | 8 | 1.00 | 5.72 | 515 | 27.8 | 1511 |
| Unoriented | 0.061 | 8 | 1.56 | 5.10 | 561 | 31.8 | 1488 |
| Unoriented | 0.230 | 8 | 6.35 | 5.63 | 1191 | 23.4 | 3747 |
| Biaxially Oriented | 0.010 | 8 | 1.13 | 14.13 | 25.0 | 22.5 | 184 |

Example 3

Comparative Data for Commercial Films

Tables 4 and Table 5 below illustrate the advantageous mechanical properties of P4HB films prepared by the methods described herein. Their tensile properties are compared with films made from an absorbable polymer, L-PLA (L-polylactic acid), unoriented P4HB films produced in this work and with unoriented P4HB films produced in a batch process.

TABLE 4

Tensile Property Comparison

| Samples | Tensile Strength kgf/mm$^2$ | Elongation at Break % | Tensile Modulus kgf/mm$^2$ | Toughness kgf/mm$^2$ |
|---|---|---|---|---|
| P4HB Unoriented Film, Batch Process See U.S. Pat. No. 6,548,569 | 5.27 | 1,000 | 66.0 | N/A |
| P4HB Melt Extruded Unoriented (Average values from Table 3) | 5.48 | 500-1200 | 27.7 | 2249 |
| P4HB Biaxially oriented | 14.13 | 25.0 | 22.5 | 184.0 |
| PLLA Film | 6.32 | 1.50 | 745.6 | 3.875 |

TABLE 5

Ball Burst Strength Comparison (1.0 inch ball, 1.75 inch opening, 300 mm/min ball speed per ASTM D6797-2)

| Samples | Thickness mm | Burst Load kgf | Burst Stress kgf/mm$^2$ | Ball displacement at break mm |
|---|---|---|---|---|
| P4HB Melt Extruded Unoriented | 0.036 | 16.14 | 14.28 | 95.3 |
| P4HB Melt Extruded Unoriented | 0.059 | 19.13 | 11.71 | 87.6 |
| P4HB Melt Extruded Unoriented | 0.226 | 70.42 | 9.92 | 83.0 |
| P4HB Biaxially Oriented | 0.01 | 3.6 | 7.22 | 22.7 |
| PLLA film | 0.100 | 4.5 | 1.88 | 3.3 |
| SurgiWrap | 0.046 | 5.38 | 3.72 | 5.7 |

We claim:

1. A non-porous film of an oriented poly-4-hydroxybutyrate polymer or a copolymer thereof,
   wherein the film has an elongation at break from 10-500%, and
   wherein the film is derived by drying the polymer or copolymer to less than 0.01% (w/w) water, melt extruding the polymer or copolymer, then orienting the film by stretching the film by more than 25% of the film's original length in one or more directions.

2. A device comprising the film of claim 1.

3. The device of claim 2 wherein the film is a component of a device selected from the group consisting of a stent, stent graft, stent coating, drug delivery device, device for temporary wound or tissue support, repair patch, tissue engineering scaffold, retention membrane, anti-adhesion membrane, tissue separation membrane, hernia repair device, device coating, cardiovascular patch, catheter balloon, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, atrial septal defect repair devices, patent foramen ovale (PFO) closure devices, left atrial appendage (LAA) closure device, pericardial patch, bulking agent, filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

4. The film of claim 1, wherein the thickness of the film is less than 10.0 mm.

5. The film of claim 1 further comprising a prophylactic, diagnostic, or therapeutic agent.

6. The film of claim 1 further comprising additives selected from the group consisting of plasticizers, nucleants, compatibilizers, porogens, radiolabelled substances, imaging agents, radiopaque markers, contrast agents, anti-oxidants, dyes, viscosity modifiers, and odor control agents.

7. A method of producing a non-porous oriented poly-4-hydroxybutyrate polymer or copolymer film, wherein the film has an elongation at break from 10-500%,
   comprising drying the polymer or copolymer to less than 0.01% (w/w) water,
   melt extruding the polymer or copolymer to form a film, and
   orienting the film by stretching the film by more than 25% of the film's original length in one or more directions.

8. The method of claim 7 further comprising forming the film into a component of a device selected from the group consisting of a stent, stent graft, stent coating, drug delivery device, device for temporary wound or tissue support, repair patch, tissue engineering scaffold, retention membrane, anti-adhesion membrane, tissue separation membrane, hernia repair device, device coating, cardiovascular patch, catheter balloon, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, atrial septal defect repair devices, patent foramen ovale (PFO) closure devices, left atrial appendage (LAA) closure device, pericardial patch, bulking agent, filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

9. A method of using a device comprising a non-porous oriented poly-4-hydroxybutyrate polymer or copolymer film,
wherein the film has an elongation at break from 10-500%,
wherein the film is derived by a continuous process of solvent casting or melt extrusion of the polymer or copolymer to form a film, followed by orienting the film by stretching the film by more than 25% of the film's original length in one or more directions,
comprising inserting or implanting the device into an individual in need thereof.

10. The method of claim 9 wherein the device is selected from the group consisting of a stent, stent graft, stent coating, drug delivery device, device for temporary wound or tissue support, repair patch, tissue engineering scaffold, retention membrane, anti-adhesion membrane, tissue separation membrane, hernia repair device, device coating, cardiovascular patch, catheter balloon, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, atrial septal defect repair devices, patent foramen ovale (PFO) closure devices, left atrial appendage (LAA) closure device, pericardial patch, bulking agent, filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

11. The film of claim 1, wherein the thickness of the film is less than 1.0 mm.

12. The film of claim 1, wherein the thickness of the film is less than 100 μm.

13. The film of claim 1, having a toughness greater than 10.0 kgf/mm$^2$.

14. The film of claim 1 having a toughness of about 184 kgf/mm$^2$ and a tensile strength of about 14.13 kgf/mm$^2$.

15. The film of claim 1, consisting of a copolymer selected from the group consisting of a copolymer of 4-hydroxybutyrate and 3-hydroxybutyrate, and a copolymer of 4-hydroxybutyrate and glycolic acid.

16. The film of claim 1, wherein the film is monoaxially or biaxially oriented.

17. The method of claim 7, consisting of a copolymer selected from the group consisting of a copolymer of 4-hydroxybutyrate and 3-hydroxybutyrate, and a copolymer of 4-hydroxybutyrate and glycolic acid.

18. The method of claim 7, wherein the film is monoaxially or biaxially oriented.

* * * * *